(12) United States Patent
Yoon et al.

(10) Patent No.: US 11,642,089 B2
(45) Date of Patent: May 9, 2023

(54) APPARATUS AND METHOD FOR CALIBRATING BIO-INFORMATION ESTIMATION MODEL, AND APPARATUS FOR ESTIMATING BIO-INFORMATION

(71) Applicant: SAMSUNG ELECTRONICS CO., LTD., Suwon-si (KR)

(72) Inventors: Seung Keun Yoon, Seoul (KR); Seung Woo Noh, Seongnam-si (KR); Chang Soon Park, Chungju-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 538 days.

(21) Appl. No.: 16/811,768

(22) Filed: Mar. 6, 2020

(65) Prior Publication Data
US 2021/0000429 A1   Jan. 7, 2021

(30) Foreign Application Priority Data
Jul. 4, 2019   (KR) .................. 10-2019-0080709

(51) Int. Cl.
*A61B 5/00*   (2006.01)
*G16H 50/50*   (2018.01)
(Continued)

(52) U.S. Cl.
CPC ............ *A61B 5/7278* (2013.01); *A61B 5/022* (2013.01); *A61B 5/02007* (2013.01);
(Continued)

(58) Field of Classification Search
None
See application file for complete search history.

(56) References Cited

U.S. PATENT DOCUMENTS 9,703,417 B2   7/2017   Taki
10,045,700 B2   8/2018   Noh et al.
(Continued)

FOREIGN PATENT DOCUMENTS

EP   3 430 991 A1   1/2019
EP   3 469 984 A1   4/2019
(Continued)

OTHER PUBLICATIONS

Bushman et al., "A Procedure for Combining Sample Correlation Coefficients and Vote Counts to Obtain an Estimate and a Confidence Interval for the Population Correlation Coefficient", Psychological Bulletin, vol. 117, No. 3, Jan. 1, 1995, pp. 530-546, XP055731059.
(Continued)

*Primary Examiner* — Yi-Shan Yang
(74) *Attorney, Agent, or Firm* — Sughrue Mion, PLLC

(57) ABSTRACT

An apparatus for calibrating a bio-information estimation model is provided. The apparatus for calibrating a bio-information estimation model includes: a data obtainer configured to obtain at least one pulse wave signal; and a processor configured to extract a plurality of feature sets, each feature set including one or more features, from each of the at least one pulse wave signal, and configured to calibrate a bio-information estimation model based on a correlation distribution of the extracted plurality of feature sets.

24 Claims, 15 Drawing Sheets

(51) Int. Cl.
  *G16H 50/30* (2018.01)
  *A61B 5/02* (2006.01)
  *A61B 5/021* (2006.01)
  *A61B 5/022* (2006.01)
  *A61B 5/024* (2006.01)
  *A61B 5/16* (2006.01)

(52) U.S. Cl.
  CPC ...... *A61B 5/02108* (2013.01); *A61B 5/02416* (2013.01); *A61B 5/165* (2013.01); *A61B 5/6843* (2013.01); *A61B 5/7246* (2013.01); *G16H 50/30* (2018.01); *G16H 50/50* (2018.01); *A61B 5/02433* (2013.01); *A61B 2560/0223* (2013.01)

(56) References Cited

U.S. PATENT DOCUMENTS

| | | | |
|---|---|---|---|
| 10,154,818 | B2 | 12/2018 | Zhang et al. |
| 2014/0187884 | A1 | 7/2014 | Addison et al. |
| 2016/0038044 | A1 | 2/2016 | Banerjee et al. |
| 2017/0112395 | A1 | 4/2017 | Kim et al. |
| 2017/0238818 | A1 | 8/2017 | Gaurav et al. |
| 2017/0258340 | A1 | 9/2017 | Przybyszewski et al. |
| 2017/0311902 | A1 | 11/2017 | Ferber et al. |
| 2018/0235487 | A1 | 8/2018 | Paul et al. |
| 2019/0104997 | A1 | 4/2019 | Kang et al. |
| 2020/0146567 | A1* | 5/2020 | Dennis ................ A61B 5/7275 |
| 2020/0229716 | A1* | 7/2020 | Schmitt ............... A61B 8/5223 |
| 2020/0375512 | A1* | 12/2020 | Lu ......................... G16H 50/70 |

FOREIGN PATENT DOCUMENTS

| | | |
|---|---|---|
| JP | 2015-0031965 A | 2/2015 |
| KR | 10-2016-0078208 A | 7/2016 |
| KR | 10-2017-0019189 A | 2/2017 |
| KR | 10-2017-0048970 A | 5/2017 |
| KR | 10-2018-0088096 A | 8/2018 |
| KR | 10-2019-0011026 A | 2/2019 |
| WO | 2019016802 A1 | 1/2019 |

OTHER PUBLICATIONS

Communication dated Sep. 25, 2020 issued by the European Intellectual Property Office in counterpart European Application No. 20171495.3.

\* cited by examiner

APPARATUS AND METHOD FOR CALIBRATING BIO-INFORMATION ESTIMATION MODEL, AND APPARATUS FOR ESTIMATING BIO-INFORMATION

CROSS-REFERENCE TO RELATED APPLICATION(S)

This application claims priority from Korean Patent Application No. 10-2019-0080709, filed on Jul. 4, 2019, in the Korean Intellectual Property Office, the entire disclosure of which is incorporated herein by reference for all purposes.

BACKGROUND

1. Field

Example embodiments of the disclosure relate to calibrating a bio-information estimation model and estimating bio-information based on the calibrated bio-information estimation model.

2. Description of Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

One or more example embodiments provide apparatuses and methods for calibrating bio-information estimation model and apparatuses and methods for estimating bio-information, in which accuracy in estimating blood pressure may be improved.

According to an aspect of an example embodiment, there is provided an apparatus for calibrating a bio-information estimation model, the apparatus including: a data obtainer configured to obtain at least one pulse wave signal; and a processor configured to extract a plurality of feature sets, each feature set including one or more features, from each of the at least one pulse wave signal, and configured to calibrate a bio-information estimation model based on a correlation distribution of the extracted plurality of feature sets with respect to reference bio-information.

The processor may be further configured to obtain an individual correlation distribution between individual one or more features included in each of the plurality of feature sets and the reference bio-information.

The processor may be further configured to combine one or more features of each of the plurality of feature sets based on the obtained individual correlation distribution, and obtain a combined correlation distribution between the combined one or more features of each of the plurality of feature sets and the reference bio-information.

The processor may be further configured to determine a weight for each of the one or more features of each of the plurality of feature sets based on the individual correlation distribution, and combine the one or more features of each of the plurality of feature sets based on the determined weight.

The processor may be further configured to obtain a correlation coefficient, related to the bio-information estimation model, based on at least one of the individual correlation distribution or the combined correlation distribution.

The correlation coefficient may include at least one of a reference feature, a scale factor, or an offset.

The data obtainer may be further configured to receive the reference bio-information, including a cuff blood pressure value, from an external device.

The processor may be further configured to obtain a predetermined number of representative waveforms from each of the at least one pulse wave signal, and extract one feature set from each of the obtained predetermined number of representative waveforms.

The processor may be further configured to obtain the predetermined number of representative waveforms from a pulse wave signal by ensemble averaging waveforms of the pulse wave signal in units of a predetermined number of bits.

The processor may be further configured to adjust at least one of the predetermined number of bits or a measurement time of the pulse wave signal, based on at least one of a user input, a user characteristic, an external environment characteristic, a bio-information estimation history, a type of bio-information to be estimated, or a computing performance of the apparatus.

The processor may be further configured to determine whether to perform calibration based on at least one of a predetermined calibration interval, a user input, a result of estimating bio-information based on the calibrated bio-information estimation model, or a bio-information estimation history.

According to an aspect of an example embodiment, there is provided a method of calibrating a bio-information estimation model, the method including: obtaining at least one pulse wave signal; extracting a plurality of feature sets, each feature set including one or more features, from each of the at least one pulse wave signal; and calibrating a bio-information estimation model based on a correlation distribution of the extracted plurality of feature sets with respect to reference bio-information.

The calibrating may include obtaining an individual correlation distribution between individual one or more features included in each of the plurality of feature sets and the reference bio-information.

The calibrating may further include: combining one or more features of each of the plurality of feature sets based on the obtained individual correlation distribution; and obtaining a combined correlation distribution between the combined one or more features of each of the plurality of feature sets and the reference bio-information.

The combining may include: determining a weight for each of the one or more features of each of the plurality of feature sets based on the individual correlation distribution; and combining the one or more features of each of the plurality of feature sets based on the determined weight.

The calibrating may further include obtaining a correlation coefficient, related to the bio-information estimation model, based on at least one of the individual correlation distribution or the combined correlation distribution.

The correlation coefficient may include at least one of a reference feature, a scale factor, or an offset.

The method may further include receiving the reference bio-information, including a cuff blood pressure value, from an external device.

The extracting the plurality of feature sets may include: obtaining a predetermined number of representative waveforms from each of the at least one pulse wave signal; and extracting one feature set from each of the obtained predetermined number of representative waveforms.

The obtaining the predetermined number of representative waveforms may include obtaining the predetermined number of representative waveforms from a pulse wave signal by ensemble averaging waveforms of the pulse wave signal in units of a predetermined number of bits.

The method may further include adjusting at least one of the predetermined number of bits or a measurement time of the pulse wave signal, based on at least one of a user input, a user characteristic, an external environment characteristic, a bio-information estimation history, a type of bio-information to be estimated, or a computing performance of an apparatus.

In an aspect of an example embodiment, there is provided an apparatus for estimating bio-information, the apparatus including: a pulse wave sensor configured to obtain pulse wave signals from an object; and a processor configured to extract a plurality of feature sets based on at least one first pulse wave signal obtained by the pulse wave sensor, configured to calibrate a bio-information estimation model based on a distribution of the extracted plurality of feature sets, and configured to estimate bio-information by using a second pulse wave signal obtained by the pulse wave sensor and the calibrated bio-information estimation model.

The pulse wave sensor may include: at least one light source configured to emit light onto the object; and at least one detector configured to receive light reflected from the object.

The processor may be configured to extract features related to the bio-information from at least one of a first pulse wave signal or the second pulse wave signal, based on at least one of heart rate information, a shape and an area of a waveform, a time value and an amplitude value of a maximum amplitude point, a time value and an amplitude value of a minimum amplitude point, or amplitude and time information of pulse waveform components of the at least one of the first pulse wave signal or the second pulse wave signal.

The processor may be configured to calibrate the bio-information estimation model based on at least one of an individual correlation distribution or a combined correlation distribution, the individual correlation distribution being between individual features of the plurality of feature sets and reference bio-information, the combined correlation distribution being between combined features, which are obtained by combining the features of the plurality of feature sets, and the reference bio-information.

The processor may be configured to obtain a correlation coefficient of the bio-information estimation model based on at least one of the individual correlation distribution or the combined correlation distribution, the correlation coefficient including at least one of a reference feature, a scale factor, or an offset.

The processor may be configured to obtain a predetermined number of representative waveforms of a first pulse wave signal by ensemble averaging waveforms of the first pulse wave signal in units of a predetermined number of bits, and extract one feature set from each of the obtained predetermined number of representative waveforms.

The bio-information may include at least one of a blood pressure, a vascular age, an arterial stiffness, an aortic pressure waveform, a vascular compliance, a stress index, and a degree of fatigue.

The apparatus may further include an output interface configured to output a processing result of the processor.

The processor may be configured to control the output interface to output information on at least one of a contact force to be applied by the object to the pulse wave sensor, a contact position of the object relative to the pulse wave sensor, and a measurement time of a pulse wave signal.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Figure 1:
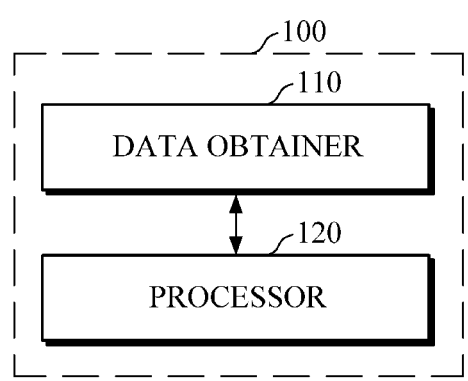
FIG. 1 is a block diagram illustrating an apparatus for calibrating a bio-information estimation model according to an example embodiment.

Details of example embodiments of the disclosure are included in the following detailed description and drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising", will be understood to imply the inclusion of stated elements but not the exclusion of any other elements. Terms, such as 'part' and 'module' denote units that process at least one function or operation and they may be implemented by using hardware, software, or a combination thereof.

Hereinafter, example embodiments of an apparatus and a method for calibrating a bio-information estimation model and an apparatus for estimating bio-information will be described in detail with reference to the accompanying drawings.

FIG. 1 is a block diagram illustrating an apparatus for calibrating a bio-information estimation model according to an example embodiment. The bio-information estimation model may be a model defined in various forms, such as a linear/non-linear function and the like, for estimating blood pressure, vascular age, arterial stiffness, aortic pressure waveform, vascular compliance, stress index, degree of fatigue, and the like. For convenience of explanation, the following description will be given using blood pressure as an example.

Referring to FIG. 1, the apparatus 100 for calibrating a bio-information estimation model (hereinafter referred to as a calibration apparatus) includes a data obtainer 110 and a processor 120. The data obtainer 110 and the processor 120 are distinguished according to their functions, and at least some of the functions of the data obtainer 110 may be performed by the processor 120.

The data obtainer 110 may obtain calibration data under the control of the processor 120. For example, the calibration data may include a pulse wave signal, including a photoplethysmogram (PPG) signal measured from a user, and reference bio-information (e.g., cuff blood pressure) measured by an external device (e.g., cuff manometer).

The data obtainer 110 may obtain the calibration data while a user is in a stable state, and may obtain a plurality of calibration data (hereinafter referred to as "multi-calibration data") by obtaining the calibration data at a plurality of times. The multi-calibration data may include a plurality of pulse wave signals and a plurality of reference bio-information items, which are obtained at respective times of obtaining the calibration data (or each calibration time).

In an example embodiment, the number of times of obtaining calibration data of the multi-calibration data may be preset. For example, the plurality of times of obtaining calibration data may have regular time intervals therebetween by considering a period of time needed for a user to return to a stable state after measuring cuff blood pressure using a cuff manometer while the user is in a stable state. In this case, the regular time interval may be a fixed value (e.g., 30 minutes) which is applied equally to all users, or a value which is adaptively adjusted for each user. However, the plurality of times are not necessarily limited to regular time intervals. For example, each time of obtaining the calibration data may be designated by a user input. Alternatively, calibration data of the multi-calibration data may be set to be obtained one or more times a day for a period of two or more days.

When obtaining the multi-calibration data, the data obtainer 110 may control a display, a speaker, a haptic module, and the like of the calibration apparatus 100 at each time, and may guide a user to measure reference bio-information and a pulse wave signal at each time. For example, the data obtainer 110 may provide a user interface through a display, and may output guide information, for guiding a user to measure the reference bio-information and the pulse wave signal, to the user interface. In an example embodiment, the display may include a touch screen configured to allow a touch input.

The data obtainer 110 may include a pulse wave sensor including a PPG sensor. The pulse wave sensor may measure a pulse wave signal from an object of a user. For example, the object may be skin tissue of the human body, and may be, for example, a body part such as the back of the hand, the wrist, fingers, and the like, at which veins or capillaries are located. However, the object is not limited thereto. For example, the object may be a body part at which arteries, such as the radial artery, are located.

The pulse wave sensor may include a light source configured to emit light onto the object, and a detector configured to detect scattered or reflected light when light emitted by the light source is scattered or reflected from body tissue of the object such as a skin surface or blood vessels of the object.

The light source may emit light in a predetermined wavelength range onto the object which is in contact with the pulse wave sensor. The predetermined wavelength range may be an infrared ray region and/or a visible ray region. The light source may include a light emitting diode (LED), a laser diode (LD), a phosphor, and/or the like, but is not limited thereto. The light source may include an LED, and may emit light of a single wavelength. Alternatively, the light source may include an array of a plurality of LEDs, in which the LEDs may emit light of the same wavelength, or at least some of the LEDs may emit light of different wavelengths.

The detector may detect light emanating from the object as light emitted by the light source is absorbed into or scattered or reflected from the tissue of the object, and may convert the intensity of the detected light into an electric signal and output the signal. The detector may include a photo diode, a photo transistor (PTr), an image sensor (e.g., CMOS image sensor), and/or the like, but is not limited thereto. For example, the detector may be provided as a photo diode or in an array of a plurality of photo diodes. When a plurality of detectors are provided, each of the plurality of detectors may be positioned at different distances from the light source, and may detect light, emitted by the light source and scattered or reflected from the tissue of the object, at different positions.

In addition, when the pulse wave sensor measures a pulse wave signal, the data obtainer 110 may display a contact position on the user interface, so that a user may accurately position the object on the pulse wave sensor. Further, the data obtainer 110 may display an intensity of force to be applied by the user's object to the pulse wave sensor during a period of time (e.g., about 45 seconds) for measuring a pulse wave signal from the object.

In another example, the data obtainer 110 may include a communication module for connection to an external device via wired or wireless communications. The data obtainer 110 may receive a user's pulse wave signal from an external device, such as an external pulse wave sensor, a wearable device, a smartphone, a tablet PC, a desktop computer, a laptop computer, and the like, through the communication module.

The communication module may perform communication by using various wired or wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and is not intended to be limiting.

The data obtainer 110 may receive reference blood pressure from a cuff manometer. For example, the data obtainer 110 may output guide information for guiding a user to measure cuff blood pressure on the user interface; and based on measurement of the cuff blood pressure by the cuff manometer, the data obtainer 110 may receive a measurement result from the user through the user interface. For example, the data obtainer 110 may output a voice command, such as "please measure your blood pressure," through a speaker and the like, and may output an image, such as an image showing a user measuring cuff blood pressure on the upper arm, on the user interface of the display.

In another example, the data obtainer 110 may control the aforementioned communication module to communicate with an external cuff manometer; and based on measurement of the cuff blood pressure by the cuff manometer, the data obtainer 110 may automatically receive a measurement result from the cuff manometer. The data obtainer 110 may output the received reference blood pressure to the user interface.

The processor 120 may determine whether to calibrate a bio-information estimation model. Upon determining to calibrate the bio-information estimation model, the processor 120 may control the data obtainer 110. For example, calibration intervals may be preset, or a user may directly or indirectly input a request for calibration. In addition, the processor 120 may determine whether to perform calibration based on a bio-information estimation result, a bio-information estimation history, and the like of an apparatus for estimating bio-information.

Furthermore, the processor 120 may receive calibration data from the data obtainer 110, and may calibrate the bio-information estimation model based on the received calibration data.

Hereinafter, examples of performing calibration by the processor 120 will be described with reference to FIGS. 2 to 3F. The following description is given as examples of calibrating the bio-information estimation model using multi-calibration data (hereinafter referred to as "multi-calibration"). However, this is merely an example and the disclosure does not exclude an example of performing calibration using calibration data obtained one at a time.

Figure 2:
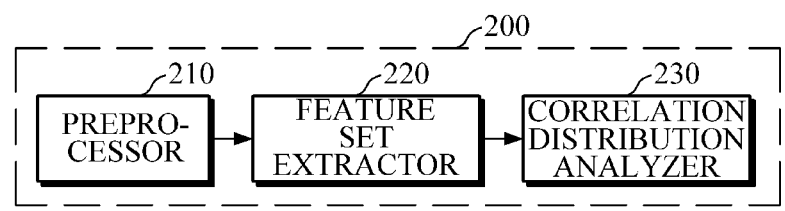
FIG. 2 is a block diagram illustrating an example of a configuration of a processor of FIG. 1.

FIG. 2 is a block diagram illustrating an example of a configuration of a processor of FIG. 1. FIGS. 3A to 3F are diagrams explaining examples of multi-calibration.

Referring to FIG. 2, a processor 200 includes a preprocessor 210, a feature set extractor 220, and a correlation distribution analyzer 230. The processor 200 may correspond to the processor 120 of FIG. 1.

The preprocessor 210 may preprocess each pulse wave signal of multi-calibration data received from the data obtainer 110. For example, the preprocessor 210 may perform preprocessing, such as detrending for normalizing each pulse wave signal and removing a trend and an offset, smoothing the signal, removing noise using a low-pass filter, and amplifying the signal.

The feature set extractor 220 may extract a plurality of feature sets from each pulse wave signal of the multi-calibration data. In this case, the number of times of extracting the feature sets may be preset, and may be adjusted based on one or more of a user input, a user characteristic, an external environment characteristic, a bio-information estimation history, a type of bio-information to be estimated, and a computing performance of the apparatus for calibrating a bio-information estimation model.

For example, if the number of times of extracting the feature sets is set to 10 and multi-calibration data are obtained by obtaining calibration data three times, a total of 30 feature sets may be obtained by extracting 10 feature sets from a pulse wave signal obtained at a first time, extracting 10 feature sets from a pulse wave signal obtained at a second time, and extracting 10 feature sets from a puke wave signal obtained at a third time. Each of the feature sets includes at least one feature. In this case, the feature is information related to bio-information. For example, in the case of estimating blood pressure, the feature may include information related to a cardiac output and a total peripheral resistance. In addition, the extracted feature sets may include features of the same type. For example, in the case of estimating blood pressure, all the feature sets may include a feature f1 related to a cardiac output and a feature f2 related to a total peripheral resistance.

The feature set extractor 220 may analyze the pulse wave signal to extract information, such as heart rate information, a shape and an area of a waveform, time and/or amplitude values of a maximum amplitude point, time and/or amplitude values of a minimum amplitude point, amplitude and/or time information of pulse waveform components constituting the pulse wave signal, and the like, and may extract features related to blood pressure by processing the extracted information and/or by combining one or more of the extracted information items.

Figure 3A:
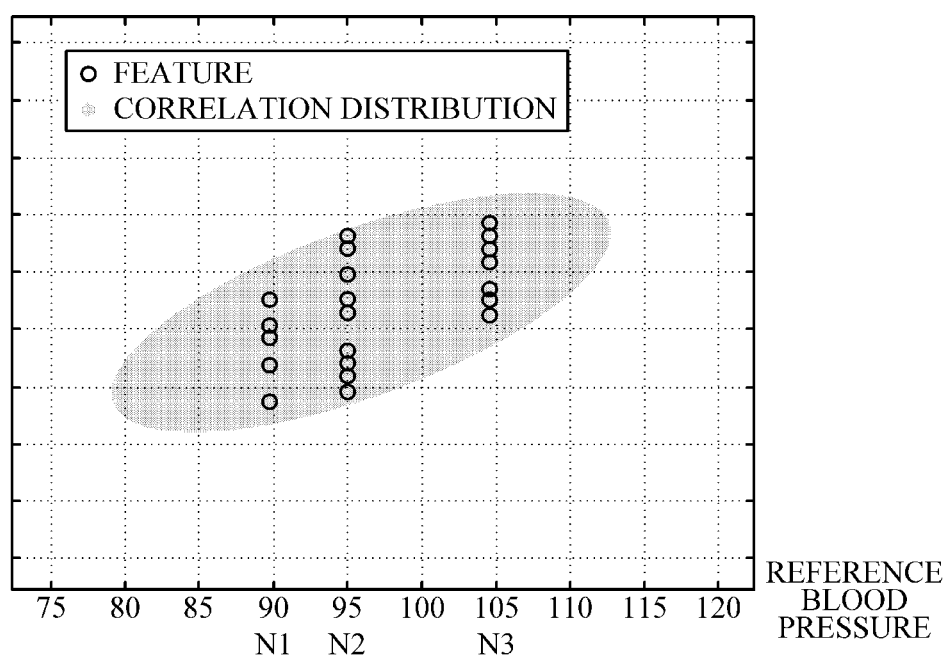
FIGS. 3A to 3F are diagrams explaining examples of calibration.
Figure 3B:
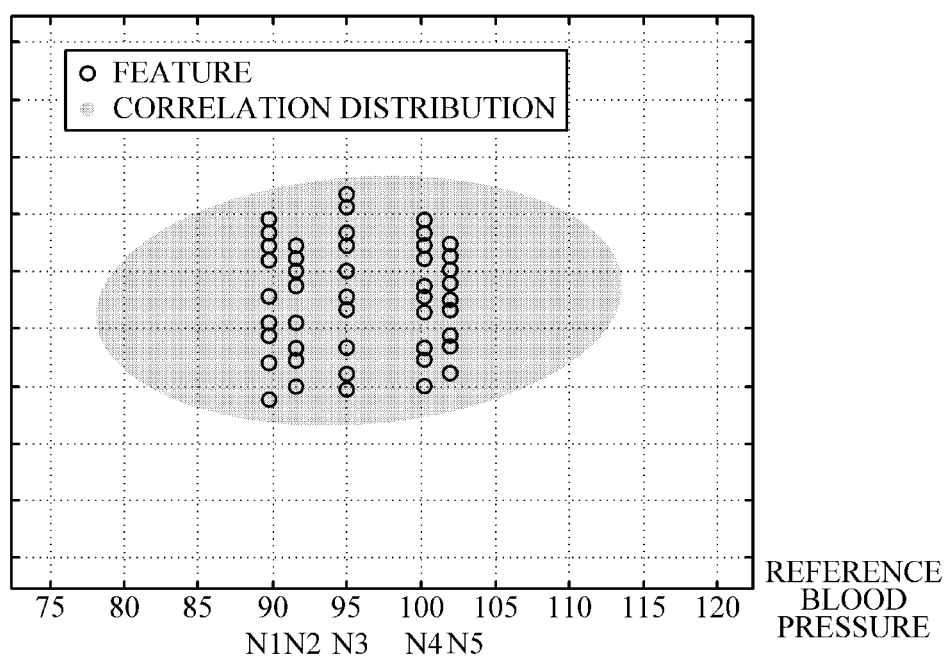

FIGS. 3A and 3B are diagrams illustrating distribution of a plurality of feature sets extracted by the feature set extractor 220.

FIG. 3A illustrates multi-calibration data obtained by obtaining calibration data three times, and a total of 30 feature sets obtained by extracting 10 feature sets from each of three pulse wave signals. Referring to FIG. 3A, N1 denotes calibration data obtained at a first time, N2 denotes calibration data obtained at a second time after a predetermined period of time elapses from the first time, and N3 denotes calibration data obtained at a third time after a predetermined period of time elapses from the second time.

Referring to FIG. 3A, a reference blood pressure level measured by a cuff manometer at the first time is about 90 mmHg. As the pulse wave signal of the first time is measured at the same time as or close to the time when the reference blood pressure is measured, it is assumed that the reference blood pressure levels of the feature sets corresponding to the first time are all equal. Accordingly, 10 feature sets extracted from the pulse wave signal of the first time are positioned corresponding to the reference blood pressure level of about 90 mmHg. Likewise, a reference blood pressure level measured at the second time is about 95 mmHg, and the 10 feature sets extracted from the pulse wave signal of the second time are positioned corresponding to the reference blood pressure level of about 95 mmHg; and a reference blood pressure level measured at the third time is about 105 mmHg, and the 10 feature sets extracted from the pulse wave signal of the third time are positioned corresponding to the reference blood pressure level of about 105 mmHg. FIG. 3A does not show all the 10 feature sets extracted at each of the three times N1, N2, and N3, since some of the feature sets are overlapped.

FIG. 3B illustrates an example in which calibration data are obtained five times N1, N2, N3, N4, and N5, and a total of 10 feature sets extracted from each pulse wave signal are positioned as described above.

Referring to FIGS. 3A and 3B, a correlation between blood pressure and feature sets may be inferred from correlation distribution of the reference blood pressure and a plurality of feature sets. FIG. 3A illustrates an example in which a correlation between the feature sets and blood pressure is relatively high, and FIG. 3B illustrates an example in which a correlation between the feature sets and blood pressure is not relatively high.

Furthermore, the feature set extractor 220 may obtain representative waveforms, the number of which corresponds to a predetermined number of feature sets to be extracted from the waveform of each pulse wave signal, and may extract one feature set from each representative waveform. FIG. 3F is a diagram illustrating an example of obtaining a representative waveform. The feature set extractor 220 may obtain the representative waveform by ensemble averaging waveforms of a pulse wave signal in units of a predetermined number of bits. In addition, by setting one window (BW) in units of a predetermined number of bits, the feature set extractor 220 may obtain a plurality of representative waveforms by sliding the window BW, as illustrated in FIG. 3F.

The feature set extractor 220 may adaptively adjust a window size of the window BW by considering predetermined reference information, e.g., a pulse wave measurement time, the number of feature sets to be extracted from each pulse wave signal, a window size (i.e., the number of bits defined in units of bits), and the like.

For example, the feature set extractor 220 may adjust the pulse wave measurement time or the number of feature sets to be extracted for each user based on a user input, a user characteristic (e.g., health condition, sex, age, etc.), an external environment characteristics (e.g., change in temperature, humidity, season, etc.), a bio-information estimation history, a type of bio-information to be estimated, a computing performance of the apparatus for calibrating a bio-information estimation model, and the like. For example, if a pulse wave measurement time is reduced, or if the number of feature sets to be extracted is increased, the feature set extractor 220 may reduce a window size so that more representative waveforms may be obtained, but the disclosure is not limited to this example embodiment.

The correlation distribution analyzer 230 may analyze correlation distribution between the plurality of feature sets extracted by the feature set extractor 220 and reference bio-information. For example, as illustrated in FIGS. 3A and 3B, the correlation distribution analyzer 230 may position the plurality of feature sets with respect to the reference blood pressure levels, and may derive correlation distribution between the feature sets and blood pressure by using appropriate analysis such as linear regression, standard deviation analysis, maximum/minimum analysis, and the like. However, the disclosure is not limited to this example embodiment.

For example, the correlation distribution analyzer 230 may obtain an individual correlation distribution based on distribution between the reference blood pressure obtained at each time and individual features of each feature set. Hereinafter, it is assumed that each feature set includes three individual features f1, f2, and f3. For example, as illustrated in FIGS. 3A and 3B, the correlation distribution analyzer 230 may obtain a correlation distribution of the first feature f1 by inferring a correlation between the first feature f1 and blood pressure based on distribution between the first feature f1 of each feature set and the reference blood pressure. Similarly, the correlation distribution analyzer 230 may obtain a correlation distribution of the second feature f2 by inferring a correlation between the second feature f2 and blood pressure based on distribution of the second feature f2 of each feature and the reference blood pressure, and obtain a correlation distribution of the third feature f3 by referring a correlation between the third feature f3 and blood pressure, based on distribution of the third feature f3 of each feature and the reference blood pressure.

In another example, the correlation distribution analyzer 230 may combine the individual features f1, f2, and f3 included in each feature set, and may obtain a combined correlation distribution between the combined features and the reference bio-information. For example, if calibration data are obtained three times, and a total of 10 feature sets are extracted each time, the correlation distribution analyzer 230 may combine three individual features f1, f2, and f3 of each feature set by using a pre-defined linear or non-linear equation, and may obtain a total of 30 combined features by obtaining 10 features each time. Further, by analyzing the total of 30 combined features as described above with reference to FIGS. 3A and 3B, the correlation distribution analyzer 230 may obtain the combined correlation distribution between the combined features and blood pressure.

Further, the correlation distribution analyzer 230 may combine the individual features based on the individual correlation distribution. For example, the correlation distribution analyzer 230 may combine the individual features by determining a weight for each of the individual features according to a correlation level between blood pressure and each of the individual features f1, f2, and f3, and by assigning the determined weight to the individual features. For example, assuming that FIG. 3A illustrates an individual correlation distribution for the first feature f1 and FIG. 3B illustrates an individual correlation distribution for the second feature f2, the first feature f1 has a relatively higher correlation level with blood pressure than the second feature f2, such that the correlation distribution analyzer 230 may assign a higher weight to the first feature f1. In this case, the correlation distribution analyzer 230 may exclude some features, having a low correlation with blood pressure, from the individual features based on the individual correlation distribution, and may combine the non-excluded features.

The correlation distribution analyzer 230 may obtain a correlation coefficient, related to a bio-information estimation model, based on the individual correlation distribution or the combined correlation distribution, and may update the bio-information estimation model based on the obtained correlation coefficient. In this case, the correlation coefficient may include, for example, a reference feature, a scale factor, an offset, and the like. Here, the reference feature indicates a feature value at a calibration time, and may be a reference value usable to obtain a relative change of a feature value at a bio-information estimation time. Further, the scale factor may be a value usable to scale a relative change of a feature value to obtain a variation in bio-information compared to that of a calibration time. In addition, an offset is a value usable to correct a bio-information variation to obtain an estimated bio-information value, and may be a measured bio-information value which is measured at a calibration time.

Figure 3C:
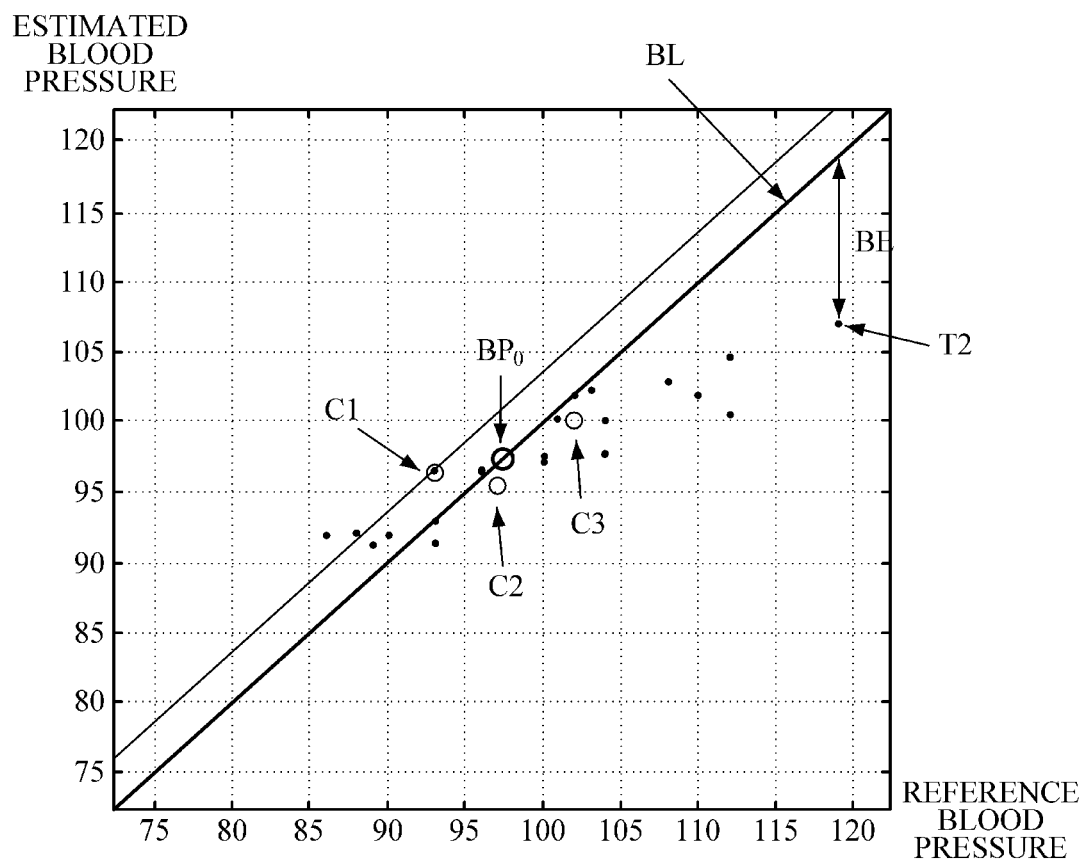
Figure 3D:
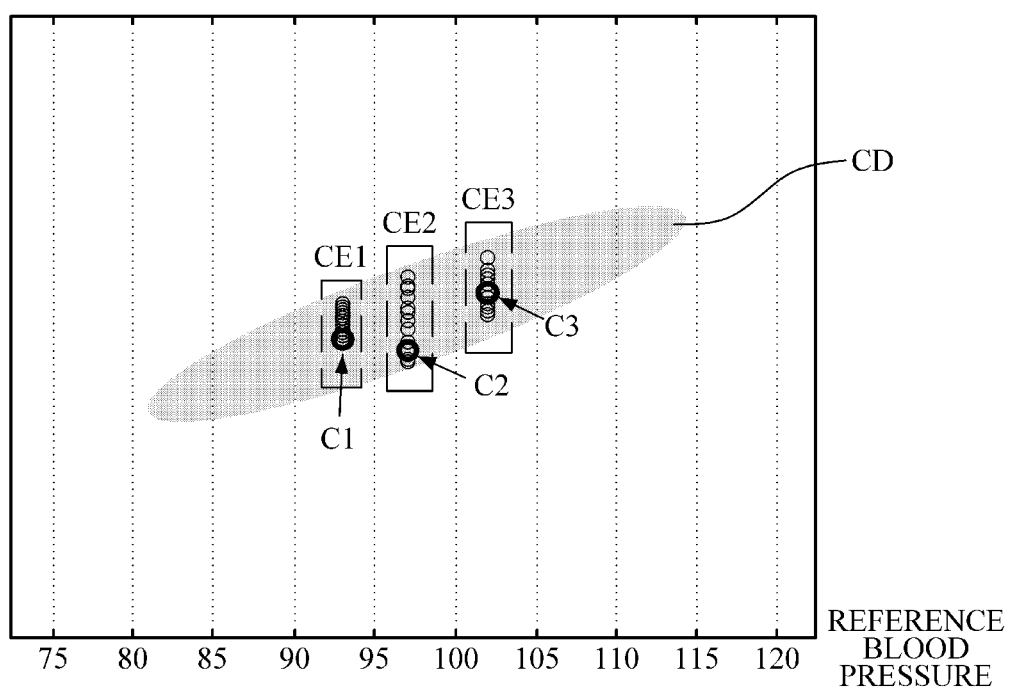
Figure 3E:
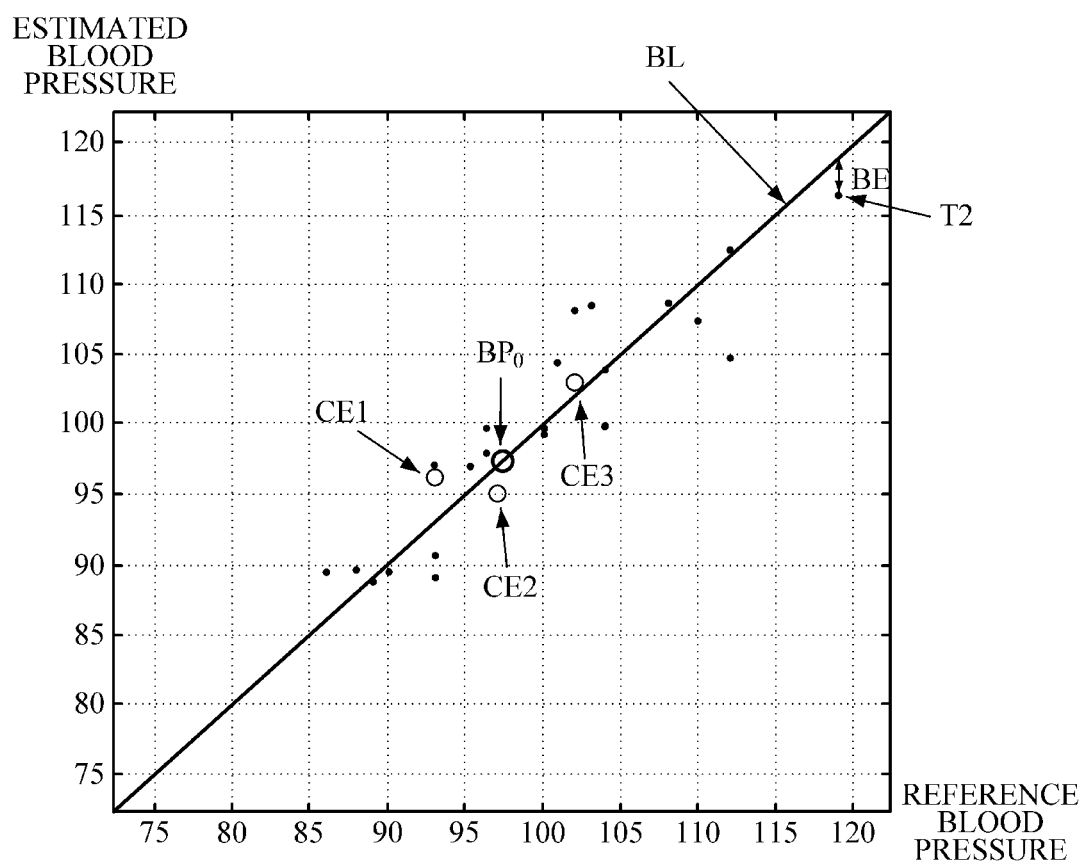
Figure 3F:
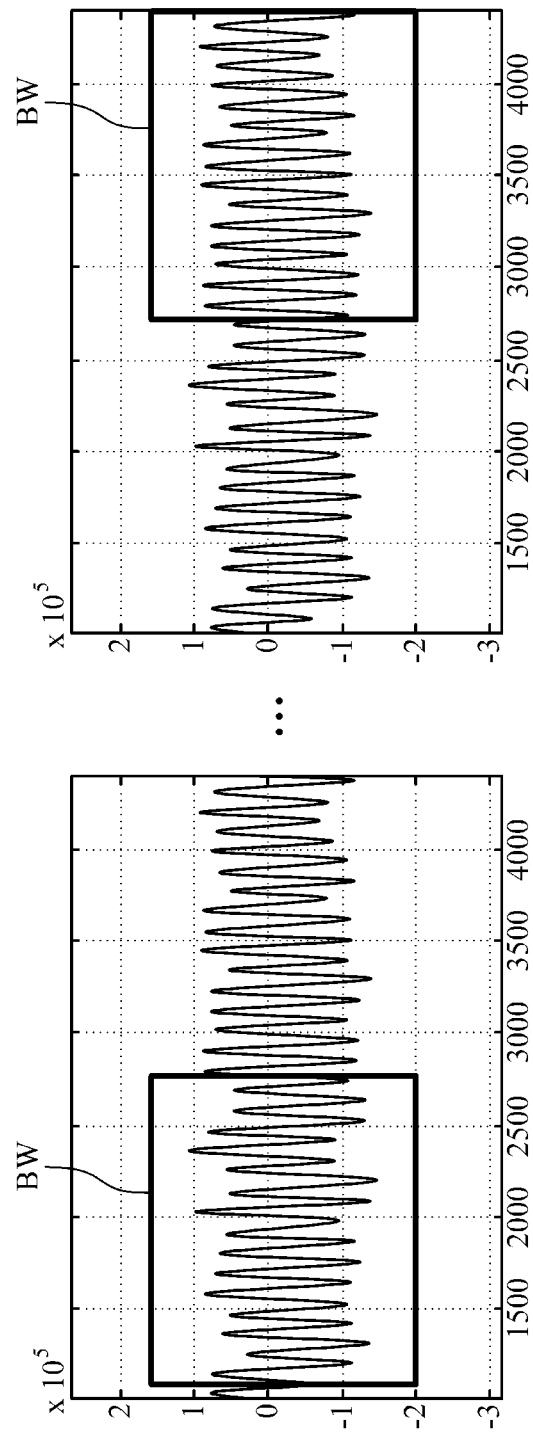

For example, FIGS. 3C to 3E are diagrams explaining a process of calibrating a blood pressure estimation model. For convenience of explanation, it is assumed that the blood pressure estimation model is defined by the following Equation 1, but is not limited thereto.

$$BP = SF \times \Delta F + OFF \qquad \text{[Equation 1]}$$

Herein, BP denotes an estimated blood pressure value at an estimation time; ΔF denotes a feature variation at the estimation time compared to a calibration time; SF denotes a scale factor. A value SF×ΔF, obtained by multiplying the feature variation ΔF and the scale factor SF, may be defined as a blood pressure variation ΔBP at the estimation time compared to the calibration time; and OFF denotes a value for correcting the blood pressure variation to obtain the estimated blood pressure value, and generally may be cuff blood pressure measured at the calibration time.

Calibration is generally performed by using calibration data obtained once. That is, the blood pressure estimation model may be updated by setting cuff blood pressure, measured at the calibration time, as an offset (OFF) of the above blood pressure estimation model, extracting a feature from a pulse wave signal measured at the calibration time, and setting the feature as a reference feature for obtaining the feature variation ΔF of the blood pressure estimation model. However, information obtained from the calibration data obtained once is not sufficient, and therefore, an error between an actual blood pressure value and an estimated blood pressure value may occur.

Referring to FIG. 3C, an X axis of a graph denotes actually measured cuff blood pressure values, and a Y axis denotes blood pressure values which are estimated using a blood pressure estimation model based on features extracted from a pulse wave signal measured at each time. The straight line (BL) denotes a line, on which the actual blood pressure values and the estimated blood pressure values coincide with each other, and as the estimated blood pressure value is located closer to the straight line, a more accurate estimation result may be obtained.

Referring to FIG. 3C, in the case where calibration is performed using calibration data obtained at a first time C1, an offset is 93 (that is, the cuff blood pressure measured at the first time C1). Further, a blood pressure variation ΔBP, which is calculated at an estimation time T2 based on a feature variation compared to the first time C1, is about 11. For example, referring to the estimated blood pressure values on the Y axis, a blood pressure level, which is estimated based on features extracted from the pulse wave signal at the first time C1, is 96; and a blood pressure level, which is estimated based on features extracted at the estimation time T2, is 107, such that it can be seen that a blood pressure variation ΔBP is 11. Accordingly, by applying 11 to the blood pressure variation ΔBP, i.e., the term of SF×ΔF in Equation 1, and applying 93 to the offset term, the estimated blood pressure value of 104 is obtained. In this case, an actual blood pressure value at the estimation time T2 is 119, such that an error between the estimated blood pressure and the actual blood pressure is 15.

Referring to FIG. 3C, if calibration data are obtained three times C1, C2, and C3 to reduce such error, calibration may be performed by using an average value of the calibration data obtained three times C1, C2, and C3. For example, reference blood pressure values of the three times C1, C2, and C3 are 93, 96, and 102 respectively, such that an offset $BP_0$ obtained by averaging the reference blood pressure values of C1-C3 is 97. The blood pressure variation ΔBP, calculated based on a feature variation at the estimation time T2, is 10. For example, referring to the estimated blood pressure values on the Y axis, blood pressure values estimated based on the features extracted at C1, C2, and C3 are 96, 95, and 100 respectively, such that an average value of the estimated blood pressure values is 97, and an estimated blood pressure value at the estimation time T2 is 107, thus obtaining a blood pressure variation of 10. Accordingly, by inputting 10 to the blood pressure variation ΔBP and inputting 97 to the offset, the estimated blood pressure value is obtained as 107. In this case, the actual blood pressure value at the estimation time T2 is 119, such that an error BE occurring between the estimated blood pressure and the actual blood pressure is 12.

As described above, in a general method of calibrating a blood pressure estimation model, even when calibration is performed using calibration data obtained once or a plurality of number of times, information for use in calibration is not sufficient, thereby causing a significant error between the estimated blood pressure and the actual blood pressure.

On the other hand, in the example embodiment, multi-calibration is performed, i.e., by extracting a plurality of feature sets from each multi-calibration data, obtaining a correlation coefficient of a blood pressure estimation model based on correlation distribution between the extracted plurality of feature sets and blood pressure, and updating the blood pressure estimation model based on the obtained correlation coefficient, error between the estimated blood pressure and the actual blood pressure may be substantially reduced, and accuracy in estimating blood pressure may be improved.

For example, referring to FIGS. 3D and 3E, if calibration data are obtained three times, a correlation coefficient of a blood pressure estimation model may be obtained by extracting a plurality of feature sets CE1, CE2, and CE3, including existing features C1, C2, and C3, from a pulse wave signal of each calibration data, and by analyzing correlation distribution CD of the extracted feature sets CE1, CE2, and CE3.

Distribution of feature sets displayed on the graph of FIG. 3D is an example of a combined correlation distribution. However, the distribution is not limited thereto, a correlation coefficient of the blood pressure estimation model may be obtained by analyzing an individual correlation distribution of one or more individual features having a high correlation.

For example, the correlation distribution analyzer 230 may obtain a linear relation between blood pressure and the combined features by using the aforementioned various analysis methods. When an offset is defined as an average value of reference blood pressure values obtained a plurality of times (e.g., three times), a reference feature may be obtained by using the linear relation. The opposite case is also possible. In another example, a correlation distribution region (CD) may be obtained using various correlation distribution analysis methods, and a reference blood pressure value and a feature at the center of gravity of the obtained region (CD) may be obtained as an offset and a reference feature, respectively. In yet another example, by obtaining a statistics value (e.g., an average value, a maximum value, a minimum value, a median value, etc.) of the combined features and a statistics value of the reference blood pressure values for each time, and by combining (e.g., averaging) the obtained three statistics values of the combined features and the obtained three statistics values of the reference blood pressure values, a reference feature and an offset may be obtained. However, these are merely examples for convenience of explanation, and are not intended to be limiting.

Referring to FIG. 3E, an offset $BP_0$ is 98, which is obtained based on the distribution of the plurality of feature sets CE1, CE2, and CE3 obtained three times as illustrated in FIG. 3D. In this case, a blood pressure variation ΔBP, calculated based on a feature variation at the estimation time T2, is 19. For example, referring to the estimated blood pressure values on the Y axis of the graph, it can be seen that an estimated blood pressure value at the calibration time (point corresponding to the offset $BP_0$) is 98, and the estimated blood pressure value at the estimation time T2 is 117, such that the calculated blood pressure variation is 19. Accordingly, by inputting 19 to the blood pressure variation ΔBP and inputting 98 to the offset in Equation 1, the estimated blood pressure value is obtained as 117. In this case, it can be seen that the actual blood pressure at the estimation time T2 is 119, showing that the error BE between the estimated blood pressure and the actual blood pressure is greatly reduced compared to the related art methods.

Figure 4:
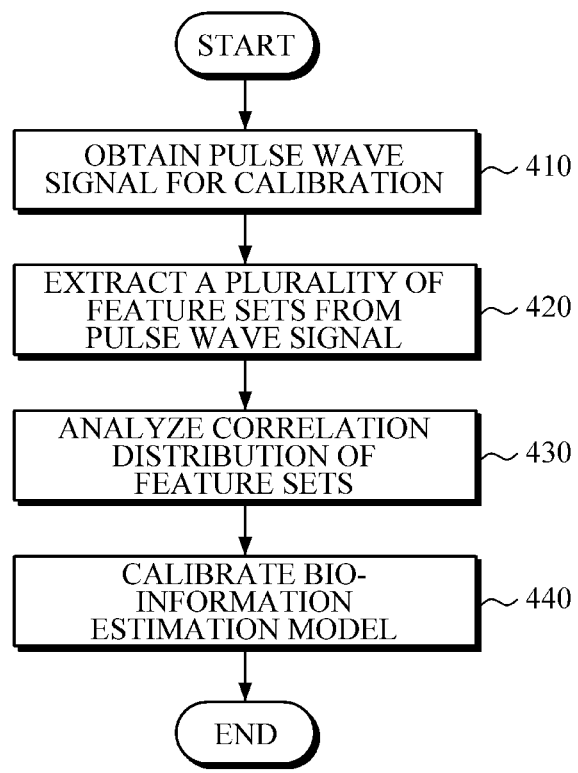
FIG. 4 is a flowchart illustrating a method of calibrating a bio-information estimation model according to an example embodiment.
Figure 5:
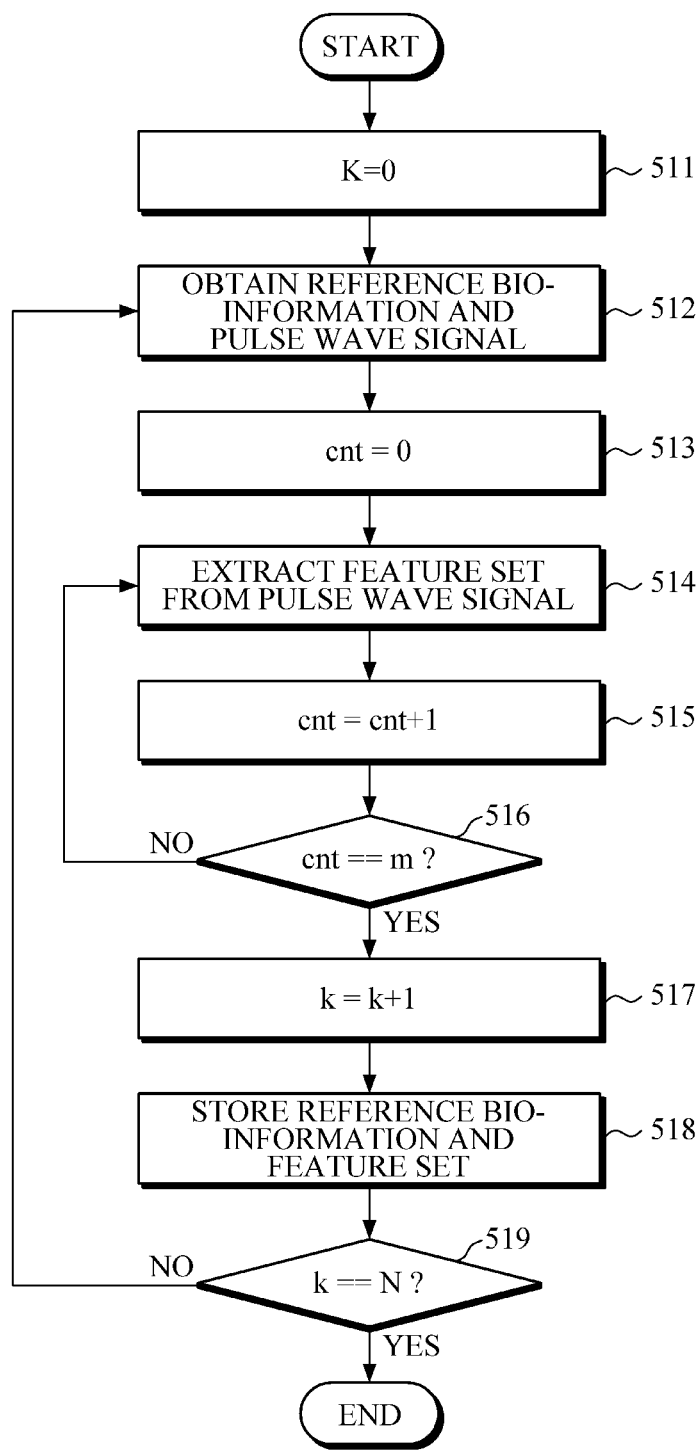
FIG. 5 is a flowchart illustrating an example of obtaining a pulse wave signal and extracting a feature set of FIG. 4.
Figure 6:
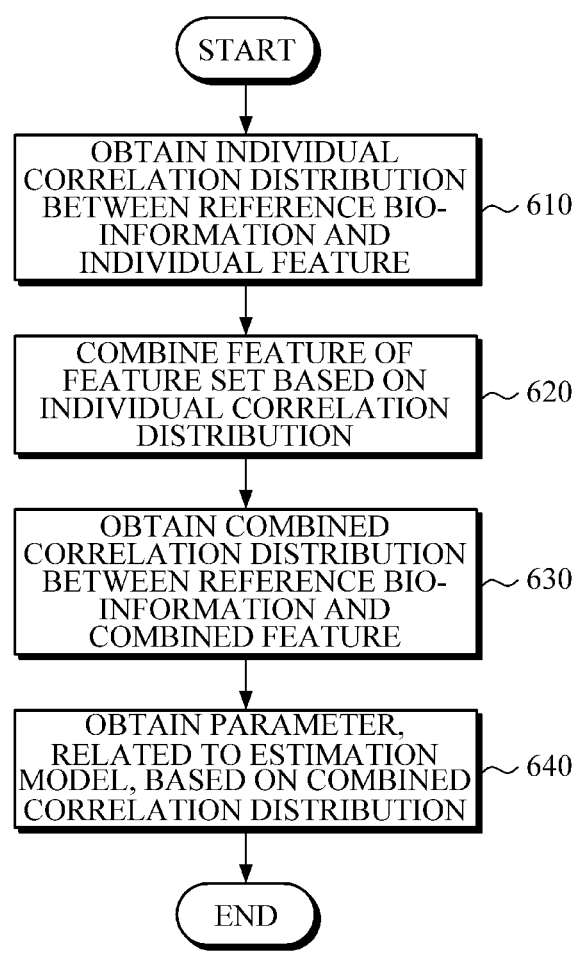
FIG. 6 is a flowchart illustrating an example of performing calibration.

FIG. 4 is a flowchart illustrating a calibration method according to an example embodiment. FIG. 5 is a flowchart illustrating an example of obtaining a pulse wave signal and extracting a feature set of FIG. 4. FIG. 6 is a flowchart illustrating an example of analyzing correlation distribution of a feature set and performing calibration.

The methods of FIGS. 4 to 6 may be performed by the aforementioned calibration apparatus, and will be briefly described in order to avoid redundancy.

Referring to FIG. 4, the calibration apparatus 100 may obtain calibration data to perform calibration in 410. The calibration data may be multi-calibration data obtained at a plurality of times. The multi-calibration data may each include a pulse wave signal and reference bio-information, which are measured at each time. In this case, the plurality of times may have regular time intervals, but are not limited thereto.

The calibration apparatus 100 may extract a plurality of feature sets from the pulse wave signals of the obtained calibration data in 420.

Referring to FIG. 5, an example of obtaining multi-calibration data will be described as an example of the operations 410 and 420.

Upon receiving a request for calibration, the calibration apparatus 100 may initialize the number k of times of obtaining calibration data in 511.

The calibration apparatus 100 may obtain the reference bio-information and the pulse wave signal in 512. For example, the calibration apparatus 100 may perform an operation (e.g., output information) to guide a user to measure cuff blood pressure. While the user measures the cuff blood pressure, if the calibration apparatus 100 may communicate with a cuff manometer, the calibration apparatus 100 may automatically receive the user's cuff blood pressure from the cuff manometer. Alternatively, the calibration apparatus 100 may provide an interface to the user to receive the cuff blood pressure from the user through the interface. Alternatively, while the user measures the cuff blood pressure, or within a predetermined period of time before or after the user measures the cuff blood pressure, the calibration apparatus 100 may measure a pulse wave signal from an object of the user, or may obtain a pulse wave signal of the user from an external device. These are merely examples and the disclosure is not limited thereto.

Subsequently, the calibration apparatus 100 may initialize the number of times (cnt) of extracting feature sets in 513, and may extract feature sets in 514 from the pulse wave signal obtained in 512. For example, by ensemble averaging waveforms of the pulse wave signal in units of a predetermined number of bits, the calibration apparatus 100 may obtain a representative waveform, and may extract feature sets from the obtained representative waveform. The feature set includes one or more features.

Next, the calibration apparatus 100 may increase the number of times (cnt) of extracting feature sets by 1, and may compare the number with a first reference value m in 516. If the number of times is not equal to the first reference value m, the calibration apparatus 100 may return to 514 to extract a next feature set. Here, the first reference value m may be a total number of feature sets to be extracted from each pulse wave signal, and may be preset. In 514, by sliding a window of a predetermined number of bits in a time running direction on the time axis of the waveforms of the pulse wave signal and by ensemble averaging waveforms of the pulse wave signal, the calibration apparatus 100 may obtain another representative waveform, and may extract a next feature set from the obtained representative waveform.

Upon comparison in 516, if the number of times (cnt) is equal to the first reference value m, the calibration apparatus 100 may terminate extracting the feature set, may increase the number k of times of obtaining the calibration data by 1 in 517, and may store, in 518, the reference bio-information and the pulse wave signal obtained in 512 and/or the feature set extracted in 514.

The calibration apparatus 100 may compare the number k of times of obtaining the calibration data with a second reference value N in 519. Upon comparison, if the number k of times of obtaining the calibration data is not equal to the second reference value N, the calibration apparatus 100 may return to 512 for obtaining next calibration data, after a predetermined period of time elapses. Upon comparison in 519, if the number k of times of obtaining the calibration data is equal to the second reference value N, the calibration apparatus 100 may terminate obtaining the calibration data. Here, the second reference value N may indicate a total number of times of obtaining the calibration data and may be preset.

Referring back to FIG. 4, the calibration apparatus 100 may perform multi-calibration upon extracting a plurality of feature sets. That is, the calibration apparatus 100 may analyze correlation distribution of the extracted feature sets in 430, and may update a bio-information estimation model based on the analysis of the correlation distribution in 440.

Referring to FIG. 6, an example of the operations 430 and 440 will be described below.

The calibration apparatus 100 may analyze correlation distribution between individual features of each feature set and reference bio-information in 610. As described above, based on the correlation distribution between each individual feature and the reference bio-information, the calibration apparatus 100 may analyze a correlation level between each individual feature and bio-information.

The calibration apparatus 100 may combine features of each feature set based on an individual correlation distribution in 620, and may obtain a combined correlation distribution between the reference bio-information and the combined features in 630. For example, the calibration apparatus 100 may infer a correlation between each feature and bio-information based on the individual correlation distribution, and may combine the features by assigning different weights to the features according to a correlation level of each feature. In an example embodiment, a feature having a low correlation may be excluded.

Subsequently, the calibration apparatus 100 may obtain a correlation coefficient, related to an estimation model, based on the combined correlation distribution in 640. For example, the calibration apparatus 100 may obtain information such as a reference feature, a scale factor, an offset, and the like. The calibration apparatus 100 may update parameters of the bio-information estimation model based on the obtained information, and may store the information as reference information for estimating bio-information.

Figure 7:
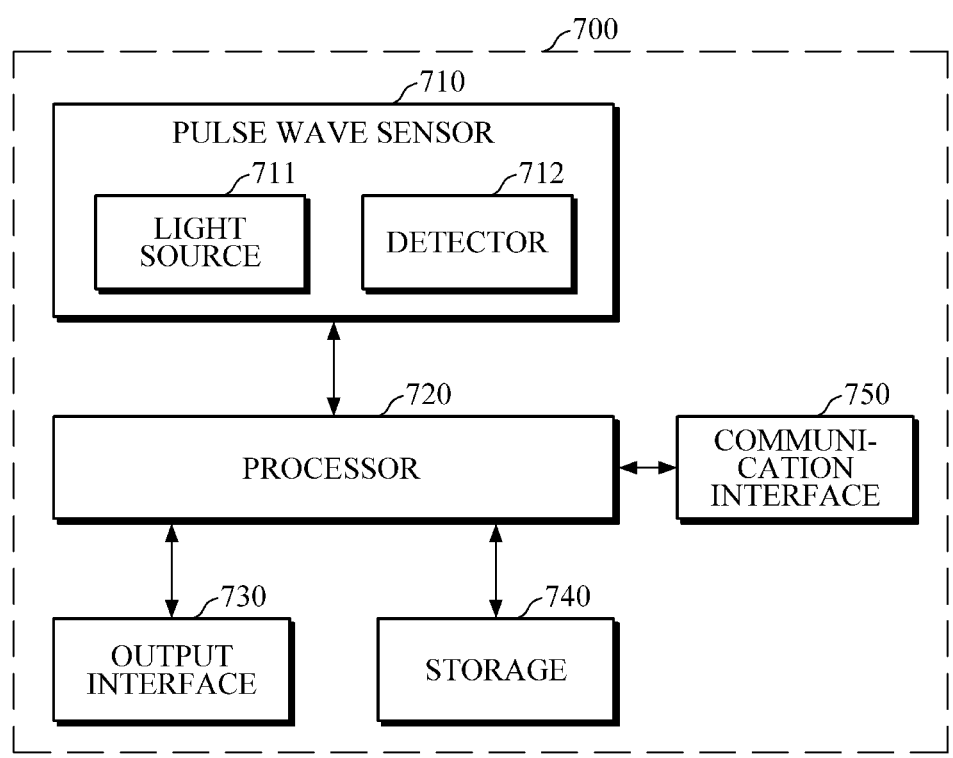
FIG. 7 is a block diagram illustrating an apparatus for estimating bio-information according to an example embodiment.
Figure 8:
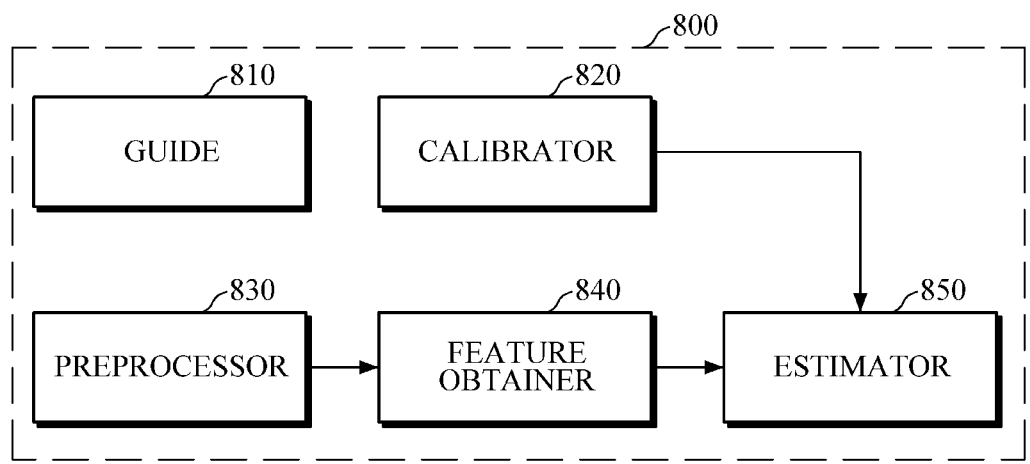
FIG. 8 is a block diagram illustrating an example of a configuration of a processor of FIG. 7.

FIG. 7 is a block diagram illustrating an apparatus for estimating bio-information according to an example embodiment. FIG. 8 is a block diagram illustrating an example of a configuration of a processor of FIG. 7. The apparatus 700 for estimating bio-information according to example embodiments of the disclosure may include the example embodiments of the calibration apparatus described above.

Referring to FIG. 7, the apparatus 700 for estimating bio-information includes a pulse wave sensor 710, a processor 720, an output interface 730, a storage 740, and a communication interface 750.

The pulse wave sensor 710 may measure a pulse wave signal, including photoplethysmography, from an object of a user. The pulse wave sensor 710 includes a light source 711 and a detector 712. The light source 711 may include one or more light emitting diodes (LED), one or more laser diodes (LD), one or more phosphors, and/or the like, and may emit light in a predetermined wavelength range onto the object of the user. The detector 712 may detect light emanating from tissue of the object when light is absorbed into or scattered or reflected from the tissue of the object. The detector 712 may include one or more photo diodes, one or more photo transistors (PTr), one or more image sensors (e.g., CMOS image sensor), and/or the like.

The processor 720 may be electrically connected to the pulse wave sensor 710. The processor 720 may control the pulse wave sensor 710 for calibration or estimating bio-information. Upon receiving a request for calibrating a bio-information estimation model, the processor 720 may control the pulse wave sensor 710 to obtain, at a plurality of times, multi-calibration data for multi-calibration as described above.

Upon receiving the pulse wave signal from the pulse wave sensor 710, the processor 720 may calibrate the bio-information estimation model or may estimate bio-information by using the received pulse wave signal.

Referring to FIG. 8, a processor 800 according to an example embodiment includes a guide 810, a calibrator 820, a preprocessor 830, a feature obtainer 840, and an estimator 850.

The guide 810 may provide a user with guide information for calibration or bio-information estimation. For example, upon receiving a request for calibration, the guide 810 may provide a user interface through the output interface 730; and may guide the user to measure reference bio-information by outputting a message, such as "please measure your blood pressure," or an image, such as showing an image of measuring blood pressure using a cuff manometer, to the user interface. Further, the guide 810 may guide the user to input the measured reference bio-information into the user interface.

In addition, upon receiving a request for calibration or a request for estimating bio-information, the guide 810 may output guide information on a contact position and a contact force between the object and the pulse wave sensor 710 (or a contact position of the object relative to the pulse wave sensor 710 and a contact force to be applied by the object to the pulse wave sensor 710), and/or a measurement time of the pulse wave signal, so that the pulse wave signal may be measured accurately.

The calibrator 820 may function as the aforementioned calibration apparatus 100. In response to a request for calibration, the calibrator 820 may obtain calibration data at least one or more times. The number of times of obtaining calibration data may be preset, and may be set to a plural number for more accurate calibration. If the number of times of obtaining calibration data is set to a plural number, the calibrator 820 may obtain multi-calibration data from the pulse wave sensor 710 and an external bio-information measuring device at predetermined time intervals. For example, the calibrator 820 may control the pulse wave sensor 710 at each time to obtain one first pulse wave signal at a time. Further, the calibrator 820 may obtain reference bio-information from the external bio-information measuring device at each time. In this case, the calibrator 820 may control the guide 810 to guide a user to measure reference bio-information and may receive the measured reference bio-information from the user through the user interface, or may control the communication interface 750 to automatically receive the reference bio-information from the external bio-information measuring device.

The calibrator 820 may extract a plurality of feature sets, including one or more features, from each first pulse wave signal. For example, the calibrator 820 may obtain a plurality of representative waveforms by ensemble averaging the entire waveforms of the first pulse wave signal while sliding a window of a predetermined number of bits. The calibrator 820 may extract one feature set from each of the obtained representative waveforms. In this case, the calibrator 820 may obtain one or more features related to bio-information from the first pulse wave signal, based on information such as heart rate information, a shape and an area of a waveform, time and amplitude values of a maximum amplitude point, time and amplitude values of a minimum amplitude point, and/or amplitude and time information of pulse waveform components.

The calibrator 820 may perform multi-calibration based on a plurality of feature sets, extracted from each pulse wave signal of multi-calibration data, and reference bio-information of the multi-calibration data. For example, by analyzing correlation distribution between the plurality of feature sets and the reference bio-information, the calibrator 820 may obtain an individual correlation distribution between individual features of each feature set and the reference bio-information, or a combined correlation distribution between combined features, obtained by combining the individual features, and the reference bio-information. Further, based on the obtained individual correlation distribution or the combined correlation distribution, the calibrator 820 may obtain a correlation coefficient related to a bio-information estimation model, e.g., a reference feature, a scale factor, an offset, and the like, and may calibrate the bio-information estimation model by using the obtained correlation coefficient. The multi-calibration is described above in detail, such that a description thereof will be omitted.

In addition, the calibrator 820 may derive correlation distribution by using cumulative calibration data obtained at calibration times prior to a current calibration time. In this case, the calibrator 820 may use previous calibration data obtained within a predetermined interval before the current time.

Upon receiving a first pulse wave signal for calibration or a second pulse wave signal for estimating bio-information, the preprocessor 830 may perform preprocessing such as smoothing, amplifying, filtering, and the like of the received signal.

The feature obtainer 840 may obtain one more features related to bio-information from the second pulse wave signal, based on information such as heart rate information, a shape and an area of a waveform, time and amplitude values of a maximum amplitude point, time and amplitude values of a minimum amplitude point, and/or amplitude and time information of pulse waveform components.

Once one or more features are extracted from the second pulse wave signal, the estimator 850 may estimate bio-information based on the extracted features by using a bio-information estimation model calibrated by the calibrator 820. Here, the bio-information may include blood pressure, vascular age, arterial stiffness, aortic pressure waveform, vascular compliance, stress index, degree of fatigue, and the like, but is not limited thereto.

For example, the estimator 850 may calculate a variation $\Delta F$ in the one or more features, extracted from the second pulse wave signal, compared to a reference feature derived by the calibrator 820, and may estimate blood pressure using the above Equation 1 in which an offset and a scale factor are calibrated. Here, the feature variation $\Delta F$ may be obtained by obtaining variations of each of the individual features f1, f2, and f3, and by assigning a weight to each of the variations and combining the weighted values. In this case, the weight may be determined based on a correlation level of individual features which is inferred from an individual correlation distribution. However, the feature variation $\Delta F$ is not limited thereto, and may be obtained by first combining the individual features f1, f2, and f3, and then obtaining a variation in the combined features.

A person of ordinary skill in the art should understand that one or more elements included in the processor 800 as described above may be implemented as computer code(s) that cause the processor to perform a corresponding function(s) of the one or more elements.

The output interface 730 may output a processing result of the processor 720. The output interface 730 may include a visual output interface such as a display and the like, a voice output interface such as a speaker and the like, or a haptic module and the like for providing information by vibrations, tactile sensation, and the like, and may provide a user with relevant information by using one or more of various output interfaces as appropriate.

For example, the output interface 730 may divide a display area into a first area and a second area; and the output interface 730 may output a bio-information estimation result, a bio-information estimation history, and the like in a first area, and may output a pulse wave signal, a plurality of feature sets, an individual correlation distribution graph and a combined correlation distribution graph as illustratively shown in FIG. 3A, graphs as illustratively shown in FIGS. 3D and 3E, and the like in a second area. In an example embodiment, the display may include a touch screen allowing a touch input; and when a user selects a bio-information estimation result at a specific time in the bio-information estimation history, the output interface 730 may output detailed information at the specific time in the second area. However, this is merely an example, and the output of information is not limited thereto.

The storage 740 may store a variety of information usable for estimating bio-information. In response to a request of the processor 720, the storage 740 may store relevant information, or may provide relevant information to the processor 720.

For example, the storage 740 may store a variety of information related to estimating bio-information, e.g., the pulse wave signal measured by the pulse wave sensor 710 and/or a processing result of the processor 720. Further, the storage 740 may store reference information, including user characteristic information such as a user's age, sex, health condition, and the like, the bio-information estimation model, the number of times of obtaining calibration data, the number of times of extracting feature sets, a window size, a measurement time of a pulse wave signal, and the like.

The storage 740 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 750 may access a communication network under the control of the processor 720, or may communicate with an external device which is connected to an accessed communication network. In this case, the external device may include a medical device such as a cuff manometer and the like, but is not limited thereto, and may include an information processing device such as a smartphone, a tablet PC, a desktop computer, a laptop computer, and the like.

For example, the communication interface 750 may receive reference information, such as cuff blood pressure and a blood pressure estimation model for estimating bio-information, from an external device such as a cuff manometer. Alternatively, the communication interface 750 may transmit the pulse wave signal measured by the pulse wave sensor 710, the pulse wave signal, the plurality of feature sets, and the bio-information estimation result which are processed by the processor 720, and various data to a user's mobile device such as a smartphone, a tablet PC, and the like.

Figure 9:
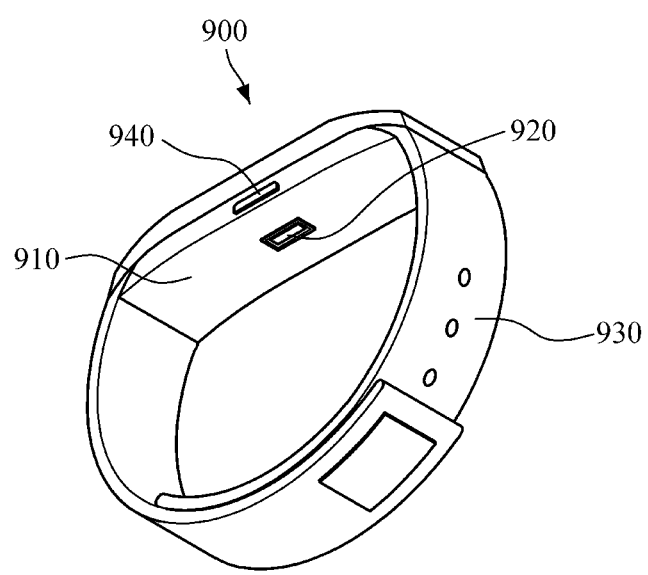
FIG. 9 is a diagram illustrating an example of a wearable device.

FIG. 9 is a diagram illustrating an example of a wearable device worn on a wrist. The calibration apparatus 100 or the apparatus 700 for estimating bio-information according to example embodiments described above may be mounted in the wearable device such as a smart watch or a smart band-type wearable device, but the apparatuses 100 and 700 are not limited thereto.

Referring to FIG. 9, the wearable device 900 includes a main body 910 and a strap 930.

The main body 910 may be formed to have various shapes, and may include various modules which are mounted inside or outside of the main body 910 to perform the aforementioned functions of performing calibration or estimating bio-information, as well as various other functions (e.g., clock, alarm, etc.). A battery may be embedded in the main body 910 or the strap 930 to supply power to the various modules of the wearable device 900.

The strap 930 may be connected to the main body 910. The strap 930 may be flexible so as to be wrapped around a user's wrist. The strap 930 may be bent in a manner that allows the strap 930 to be detached from the main body 910 or may be formed (e.g., as a band) that is not detachable from the main body 910. Air may be injected into the strap 930 or an airbag may be included in the strap 930, so that the strap 930 may have elasticity according to a change in pressure applied to the wrist, and the change in pressure of the wrist may be transmitted to the main body 910.

The main body 910 may include a pulse wave sensor 920 for measuring a pulse wave signal. The pulse wave sensor 920 may be mounted on one surface of the main body 910 which comes into contact with the user's wrist when the main body 910 is worn on a user's wrist. The pulse wave sensor 920 may include a light source for emitting light to the wrist and a detector for detecting light scattered or reflected from body tissue such as a skin surface, blood vessels, and the like.

In addition, a processor may be mounted in the main body 910, and may be electrically connected to the various modules of the wearable device 900 to control operations thereof.

In response to a request for calibration, the processor may control the pulse wave sensor 920. In this case, the request for calibration may be input from a user, or may be automatically generated at predetermined intervals. In response to the request for calibration, the processor controls the pulse wave sensor 920 to obtain a pulse wave signal for calibration, and may obtain reference bio-information from an external bio-information measuring device. The processor may obtain the calibration data a number of times at a plurality of time points.

The processor may calibrate a bio-information estimation model by using the obtained calibration data. The method of calibrating a bio-information estimation model is described above in detail, such that a description thereof will be omitted.

Further, in response to a request for estimating bio-information, the processor may control the pulse wave sensor 920 to acquire a pulse wave signal, and may estimate bio-information by using the acquired pulse wave signal and the calibrated bio-information estimation model. A detailed description of the estimation of bio-information will be omitted.

The display may be mounted on a front surface of the main body 910, and may be a touch panel that allows a touch input. The display may receive a touch input from a user, may transmit the received touch input to the processor, and may display a processing result of the processor. For example, the display may display an estimated bio-information value, and may display additional information, such as a bio-information estimation history, a change in health condition, warning information, and the like, along with the estimated value.

A storage, which stores the processing result of the processor and a variety of information, may be mounted in the main body 910. In this case, the variety of information may include information related to estimating bio-information, as well as information related to other functions of the wearable device 900.

In addition, the main body 910 may include a manipulator 940 which receives a user's command and transmits the received command to the processor. The manipulator 940 may include a power button to input a command to turn on/off the wearable device 900.

A communication interface, which communicates with an external device, may be mounted in the main body 910. The communication interface may transmit a bio-information estimation result to an external device, so as to output the estimation result through the external device, e.g., an output interface of a user's mobile terminal, or to store the estimation result in a storage of the external device. Furthermore, the communication interface may receive information for supporting various other functions of the wearable device 900 and the like from the external device.

Figure 10:
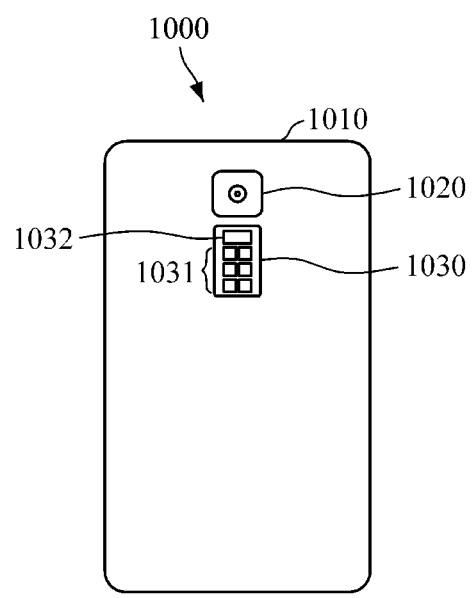
FIG. 10 is a diagram illustrating an example of a smart device.

FIG. 10 is a diagram illustrating an example of a smart device, to which embodiments of the calibration apparatus 100 or the apparatus 700 for estimating bio-information described above are applied. In this case, the smart device may be a smartphone and a tablet PC, but is not limited thereto.

Referring to FIG. 10, the smart device 1000 may include a main body 1010 and a pulse wave sensor 1030 mounted on a surface of the main body 1010. The pulse wave sensor 1030 may include one or more light sources 1031 and a detector 1032. As described above, the pulse wave sensor 1030 may be mounted on a rear surface of the main body 1010, but is not limited thereto, and may be configured in combination with a fingerprint sensor or a touch panel, which is mounted on a front surface of the main body 1010.

Further, a force sensor may be included in the main body 1010. When a user touches the pulse wave sensor with a finger and the like and applies force thereto, the force sensor may measure the force and may transmit the measurement result to the processor.

A display may be mounted on a front surface of the main body 1010. The display may visually display a bio-information estimation result and the like. The display may include a touch panel, and may receive information input through the touch panel and transmit the received information to the processor.

An image sensor 1020 may be mounted in the main body 1010. When a user's finger approaches the pulse wave sensor 1030 to measure a pulse wave signal, the image sensor 1020 may capture an image of the finger and may transmit the captured image to the processor. In this case, based on the image of the finger, the processor may identify a relative position of the finger with respect to an actual position of the pulse wave sensor 1030, and may provide the relative position of the finger to the user through the display, so as to guide a user to accurately contact the pulse wave sensor 1030 with the finger.

The processor may calibrate the bio-information estimation model and may estimate bio-information by using the pulse wave signal measured by the pulse wave sensor 1030 and the calibrated bio-information estimation model, which is described above in detail and a description thereof will be omitted.

The disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the disclosure can be readily deduced by programmers in the technical field to which the invention pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

Although a few embodiments have been shown and described, it would be appreciated by those skilled in the art that changes may be made in example embodiments without departing from the principles and spirit of the disclosure, the scope of which is defined in the claims and their equivalents.

What is claimed is:

1. An apparatus for calibrating a bio-information estimation model, the apparatus comprising:
   a pulse wave sensor configured to obtain at least one pulse wave signal; and
   a processor configured to:
   extract a plurality of feature sets from each of the at least one pulse wave signal, each feature set of the plurality of feature sets including one or more features;
   obtain an individual correlation distribution between an individual feature of the one or more features included in each of the plurality of feature sets and reference bio-information;
   combine one or more individual features of a feature set, among the plurality of feature sets, based on the obtained individual correlation distribution of each individual feature;
   obtain a combined correlation distribution between the combined one or more individual features and the reference bio-information;
   calibrate a bio-information estimation model based on the combined correlation distribution; and
   estimate bio-information based on the calibrated bio-information estimation model.

2. The apparatus of claim 1, wherein the processor is further configured to determine a weight for each of the one or more individual features of each of the plurality of feature sets based on the individual correlation distribution, and combine the one or more individual features of each of the plurality of feature sets based on the determined weight.

3. The apparatus of claim 1, wherein the processor is further configured to obtain a correlation coefficient, related to the bio-information estimation model, based on the combined correlation distribution.

4. The apparatus of claim 3, wherein the correlation coefficient comprises at least one of a feature value of a reference feature, a scale factor, or an offset.

5. The apparatus of claim 1, wherein the pulse wave sensor is further configured to receive the reference bio-information, including a cuff blood pressure value, from an external device.

6. The apparatus of claim 1, wherein the processor is further configured to obtain a predetermined number of representative waveforms from each of the at least one pulse wave signal, and extract one feature set from each of the obtained predetermined number of representative waveforms.

7. The apparatus of claim 6, wherein the processor is further configured to obtain the predetermined number of representative waveforms from a pulse wave signal by ensemble averaging waveforms of the pulse wave signal in units of a predetermined number of bits.

8. The apparatus of claim 7, wherein the processor is further configured to adjust at least one of the predetermined number of bits or a measurement time of the pulse wave signal, based on at least one of a user input, a user characteristic, an external environment characteristic, a bio-information estimation history, a type of bio-information to be estimated, or a computing performance of the apparatus.

9. The apparatus of claim 1, wherein the processor is further configured to determine whether to perform calibration based on at least one of a predetermined calibration interval, a user input, a result of estimating bio-information based on the calibrated bio-information estimation model, or a bio-information estimation history.

10. A method of calibrating a bio-information estimation model, the method comprising:
    obtaining at least one pulse wave signal;
    extracting a plurality of feature sets, each feature set of the plurality of feature sets including one or more features, from each of the at least one pulse wave signal; and
    calibrating a bio-information estimation model based on a correlation distribution of the extracted plurality of feature sets with respect to reference bio-information,
    wherein the calibrating comprises:
    obtaining an individual correlation distribution between an individual feature included in each of the plurality of feature sets and the reference bio-information,
    combining one or more individual features of a feature set, among the plurality of feature sets, based on the obtained individual correlation distribution of each individual feature,
    obtaining a combined correlation distribution between the combined one or more individual features and the reference bio-information,
    calibrating the bio-information estimation model based on the combined correlation distribution, and
    estimating bio-information based on the calibrated bio-information estimation model.

11. The method of claim 10, wherein the combining comprises:
    determining a weight for each of the one or more individual features of each of the plurality of feature sets based on the individual correlation distribution; and
    combining the one or more individual features of each of the plurality of feature sets based on the determined weight.

12. The method of claim 10, wherein the calibrating further comprises obtaining a correlation coefficient, related to the bio-information estimation model, based on the combined correlation distribution.

13. The method of claim 12, wherein the correlation coefficient comprises at least one of a feature value of a reference feature, a scale factor, or an offset.

14. The method of claim 10, further comprising receiving the reference bio-information, including a cuff blood pressure value, from an external device.

15. The method of claim 10, wherein the extracting the plurality of feature sets comprises:
  obtaining a predetermined number of representative waveforms from each of the at least one pulse wave signal; and
  extracting one feature set from each of the obtained predetermined number of representative waveforms.

16. The method of claim 15, wherein the obtaining the predetermined number of representative waveforms comprises obtaining the predetermined number of representative waveforms from a pulse wave signal by ensemble averaging waveforms of the pulse wave signal in units of a predetermined number of bits.

17. The method of claim 16, further comprising adjusting at least one of the predetermined number of bits or a measurement time of the pulse wave signal, based on at least one of a user input, a user characteristic, an external environment characteristic, a bio-information estimation history, a type of bio-information to be estimated, or a computing performance of an apparatus.

18. An apparatus for estimating bio-information, the apparatus comprising:
  a pulse wave sensor configured to obtain pulse wave signals from an object; and
  a processor configured to:
  extract a plurality of feature sets based on at least one first pulse wave signal obtained by the pulse wave sensor;
  obtain a combined correlation distribution between combined features of a feature set, which are obtained by combining the features based on an individual correlation distribution of each feature, and reference bio-information, wherein the individual correlation distribution of a feature is between the feature, included in the plurality of feature sets, and the reference bio-information;
  obtain a correlation coefficient of a bio-information estimation model based on the combined correlation distribution, the correlation coefficient including at least one of a feature value of a reference feature, a scale factor, or an offset;
  calibrate the bio-information estimation model based on the obtained correlation coefficient; and
  estimate bio-information by using a second pulse wave signal obtained by the pulse wave sensor and the calibrated bio-information estimation model.

19. The apparatus of claim 18, wherein the pulse wave sensor comprises:
  at least one light source configured to emit light onto the object; and
  at least one detector configured to receive light reflected from the object.

20. The apparatus of claim 18, wherein the processor is further configured to extract features related to the bio-information from at least one of a first pulse wave signal or the second pulse wave signal, based on at least one of heart rate information, a shape and an area of a waveform, a time value and an amplitude value of a maximum amplitude point, a time value and an amplitude value of a minimum amplitude point, or amplitude and time information of pulse waveform components of the at least one of the first pulse wave signal or the second pulse wave signal.

21. The apparatus of claim 18, wherein the processor is further configured to obtain a predetermined number of representative waveforms of a first pulse wave signal by ensemble averaging waveforms of the first pulse wave signal in units of a predetermined number of bits, and extract one feature set from each of the obtained predetermined number of representative waveforms.

22. The apparatus of claim 18, wherein the bio-information comprises at least one of a blood pressure, a vascular age, an arterial stiffness, an aortic pressure waveform, a vascular compliance, a stress index, and a degree of fatigue.

23. The apparatus of claim 18, further comprising an output interface configured to output a processing result of the processor.

24. The apparatus of claim 23, wherein the processor is further configured to control the output interface to output information on at least one of a contact force to be applied by the object to the pulse wave sensor, a contact position of the object relative to the pulse wave sensor, and a measurement time of a pulse wave signal.

* * * * *